| (12) | United States Patent | (10) Patent No.: US 11,690,917 B1 |
|---|---|---|
| | Zhang | (45) Date of Patent: Jul. 4, 2023 |

(54) METHODS AND COMPOSITIONS FOR A UNIVERSAL AND LONG-LASTING VACCINE

(71) Applicant: Gongyi Zhang, Englewood, CO (US)

(72) Inventor: Gongyi Zhang, Englewood, CO (US)

( * ) Notice: Subject to any disclaimer, the term of this patent is extended or adjusted under 35 U.S.C. 154(b) by 0 days.

(21) Appl. No.: 17/751,208

(22) Filed: May 23, 2022

(51) Int. Cl.
| *A61K 39/12* | (2006.01) |
| *A61P 31/12* | (2006.01) |
| *A61P 37/04* | (2006.01) |
| *C07K 7/06* | (2006.01) |
| *A61K 38/08* | (2019.01) |
| *A61K 47/64* | (2017.01) |
| *A61K 47/08* | (2006.01) |
| *A61K 39/215* | (2006.01) |
| *A61K 39/145* | (2006.01) |
| *A61P 31/16* | (2006.01) |
| *A61K 39/00* | (2006.01) |

(52) U.S. Cl.
CPC .......... *A61K 47/646* (2017.08); *A61K 39/145* (2013.01); *A61K 39/215* (2013.01); *A61K 47/08* (2013.01); *A61P 31/16* (2018.01); *A61K 2039/5254* (2013.01); *A61K 2039/54* (2013.01); *A61K 2039/545* (2013.01); *A61K 2039/55511* (2013.01)

(58) Field of Classification Search
CPC ........ A61K 2039/60; A61K 2039/6075; A61K 39/12; A61K 39/215; C07K 14/005
See application file for complete search history.

(56) References Cited

U.S. PATENT DOCUMENTS

| 5,578,308 A | 11/1996 | Capiau et al. |
| 6,355,246 B1 | 3/2002 | Kruger et al. |
| 2006/0160101 A1 | 7/2006 | Poulet et al. |

OTHER PUBLICATIONS

Delrue et al., "Inactivated virus vaccines from chemistry to prophylaxis: merits, risks and challenges", Expert Rev. Vaccines, 2012, 11(6):695-719.*

Zhang, Wei, et al., "The Optimal Concentration of Formaldehyde is Key to Stabilizing the Pre-Fusion Conformation of Respiratory Syncytial Virus Fusion Protein", Viruses, 2019, 11 (7): 1-14 (14 pages).

Greaney, et al., "Antibodies Elicited by mRNA-1273 Vaccination Bind More Broadly to the Receptor Binding Domain Than do those From SARS-CoV-2 Infection", Science Translational Medicine, vol. 13, 12 pages, Jun. 30, 2021.

Piccoli, et al., "Mapping Neutralizing and Immunodominant Sites on the SARS-CoV-2 Spike Receptor-Binding Domain by Structure-Guided High-Resolution Serology", Cell, vol. 183, pp. 1024-1042, Nov. 12, 2020, Elsevier Inc.

Reid, "The Sterways Process; A New Approach to Inactivating Viruses Using Gamma Radiation", Biologicals, vol. 26, pp. 125-130,1998, The International Association of Biological Standardization.

* cited by examiner

*Primary Examiner* — Barry A Chestnut

(74) *Attorney, Agent, or Firm* — Dorsey & Whitney LLP

(57) ABSTRACT

To develop a universal and long-lasting influenza or other pathogens vaccine has been a mission impossible goal in the life science and health field. Applicants disclose, herein, vaccines prepared against SARS-COV-2, an influenza A strain vaccine prepared from a 1934 influenza virus (A/PR/8/34 H1N1, Puerto Roca, 1934), and an influenza B strain vaccine prepared from a 1940 influenza virus. The disclosed vaccine induces production of broadly neutralizing antibodies in mice. The presently disclosed vaccine is able to inhibit two other influenza A strains: a 2009 influenza H1N1 virus collected from Los Angeles (A/California/07/2009) and a 2014 influenza H3N2 virus collected from Hong Kong (A/Hongkong/4801/2014). Applicants also describe an influenza B strain vaccine prepared from a B strain virus from a 1940 patient in USA (B/L11/40). The B strain vaccine also produced broadly neutralizing antibodies, in this case against a B strain from Colorado 2017 (B/Colorado/2017). Applicant's methods and compositions are not only useful in creating influenza vaccines with broad activity against other influenza subtypes but also be efficient to generate long-lasting SARS-CoV-2 vaccines against emerging new variants either through recombined protein antigens from SARS-CoV-2 or inactivated SARS-CoV-2 virus.

20 Claims, 10 Drawing Sheets

Specification includes a Sequence Listing.

```
SARS-CoV-2 RBD 387  LNDLCFTNVYADSFVIRGDEVRQIAPGQTGKIADYNYKLPDDFTGCVIAWN 437
SARS-CoV   RBD 374  LNDLCFSNVYADSFVVKGDDVRQIAPGQTGVIADYNYKLPDDFMGCVLAWN 424
                    * * ***    **    *  ******  ********** *   ** ***
                                                    *
SARS-CoV-2 RBD 438  SNNLDSKVGGNYNYLYRLFRKSNLKPFERDISTEIYQAGSTPCNGVEGFNC 488
SARS-CoV   RBD 425  TRNIDATSTGNYNYKYRYLRHGKLRPFERDISNVPFSPDGKPCTP-PALNC 474
                    * *    ******* ** *   ********     *  *** *  * **

SARS-CoV-2 RBD 489  YFPLQSYGFQPTNGVGYQPYRVVVLSFE 516
SARS-CoV   RBD 475  YWPLNDYGFYTTTGIGYQPYRVVVLSFE 502
                    * ** *  *    * *************

SARS-CoV-2 (P0DTC2, SPIKE_SARS2, PDB ID: 6M0J)
SARS-CoV   (P59594, SPIKE_CVHSA, PDB ID: 2AJF)
```

FIG 5

METHODS AND COMPOSITIONS FOR A UNIVERSAL AND LONG-LASTING VACCINE

FIELD

The disclosed processes, methods, and systems are directed to novel compositions and methods for stabilizing protein structure and manufacturing of vaccines, including vaccines for treatment and prevention of COVID-19 caused by coronavirus, SARS-CoV-2.

SEQUENCE LISTING

The instant application contains a Sequence Listing which has been submitted electronically in ASCII format and is hereby incorporated by reference in its entirety. Said ASCII copy, created on 5 Aug. 2021, is named P299021US01_508953_00004_ST25.TXT and is 2770 bytes in size.

BACKGROUND

Several factors may hamper production of effect vaccines or inhibit native viruses from inducing production of broadly neutralizing antibodies. First, due to the high mutagenesis rate of viruses, such as coronaviruses and influenza viruses, many common viral antigens may be buried or are not easily accessible to B cells in GC. Second, due to the instability of protein antigens (protein antigens are unstable either in vitro or in vivo) in vivo, follicular dendritic cells (FDCs) may not be able to present native form antigens anymore when needed (antigens have been denatured or digested in vivo). Third, traditional processes for preparing vaccine, especially where formalin or beta-propiolactone is used, results in denaturation of the native structure of viral antigens. Overall, it is difficult for FDCs to present the common antigens to B cells for further maturation and production of broadly neutralizing antibodies, it also effects the formation of final protective memory T cells. Moreover, current methods for producing vaccines are costly and very time consuming, often requiring years to develop and produce a viable vaccine.

To overcome these obstacles, Applicants describe, herein, a novel method of preparing and presenting stable antigens to FDCs during the period of time of B cells class switching and somatic hypermutation so as to generate long lasting broadly neutralizing IgGs producing plasma B cells, memory B cells, memory T cells to protect human beings against future infections of the similar types of pathogens.

SUMMARY

In one aspect, method for preparing a vaccine are disclosed, the methods include combining a dialdehyde/di-imidoester with a pathogen, contacting the dialdehyde/di-imidoester with proteins from the pathogen, and allowing the dialdehyde/di-imidoester to form intra-protein bonds to create dialdehyde/di-imidoester-modified pathogen proteins, removing or reacting dialdehyde/di-imidoester not bonded to protein, isolating the dialdehyde/di-imidoester-modified pathogen proteins, and combining the dialdehyde/di-imidoester-modified pathogen proteins with an adjuvant.

In another aspect, a method of creating a vaccine from a virus is disclosed, includes contacting the virus with a first dialdehyde/di-imidoester, incubating the virus and the first dialdehyde/di-imidoester for a first time period, to allow viral proteins to crosslink to form a cross-linked mixture, adding beta-propiolactone or formaldehyde to the mixture, incubating the mixture for a second time period, allowing beta-propiolactone or formaldehyde to inactivate live virus in the mixture, and thereby creating a killed virus vaccine. alternatively, the first dialdehyde/di-imidoester treated virus is inactivated through Gamma ray radiation.

In another aspect, a method of immunizing a subject is disclosed, the method includes injecting a subject with a dialdehyde/di-imidoester-modified pathogen protein, injecting the subject a second time and third time with the dialdehyde/di-imidoester-modified pathogen protein.

In another aspect, methods for preparing a vaccine are disclosed, the methods comprising several homobifunctional crosslinking agents of a short chain with aldehyde or imidoester at both ends, dialdehyde and di-imidoester respectively. combining dialdehyde or di-imidoester with a pathogen; contacting the dialdehyde/di-imidoester with proteins from the pathogen, and allowing the dialdehyde or the di-imidoester to form intra-protein bonds to create dialdehyde/di-imidoester-modified pathogen proteins; removing or reacting dialdehyde/di-imidoester not bonded to protein; isolating the dialdehyde/di-imidoester-modified pathogen proteins; and combining the dialdehyde/di-imidoester-modified pathogen proteins with an adjuvant. In many embodiments, the dialdehyde and the di-imidoester comprise 4 or more carbons. In many embodiments, the dialdehyde may comprise 4, 5, 6, 7, 8, 9, or 10 carbons, and two oxygens, for example the dialdehyde may be selected from glutaraldehyde, dialdehyde, or combinations thereof; and the di-imidoester may be selected from adipimidic acid dimethyl ester (DMA), dimethyl suberimidate (DMS), dimethyl pimelimidate (DMP), bis(sulfosuccinimidyl) suberate (BS3), or combinations. In many embodiments, the concentration of protein combined with the dialdehyde/di-imidoester may be less than about 1.0 mg/ml, for example less than about 0.1 mg/ml. The pathogen, in many embodiments, may be selected from a virus, bacterium, fungus, for example a virus selected from coronavirus, influenza, retrovirus, or rhinovirus. In some embodiments, the pathogen may be influenza or SARS-COV-2. In many embodiments the dialdehyde/di-imidoester may be one or more of glutaraldehyde, SB3, DMA, DMS, and DMP.

Also disclosed are methods of immunizing a subject, the method comprising injecting a subject with a dialdehyde/di-imidoester-modified pathogen protein; and injecting the subject a second time with the dialdehyde/di-imidoester-modified pathogen protein, wherein the subject is a mammal or avian, for example a mammal or avian selected from a human, a cow, a pig, horse, cat, dog, bird, or chicken. In many embodiments, the dialdehyde/di-imidoester may be a dialdehyde/di-imidoester comprising 4 or more carbons. In many embodiments, the dialdehyde/di-imidoester may comprise a molecule with 4, 5, 6, 7, 8, 9, or 10 carbons, and two oxygens, for example a dialdehyde selected from glutaraldehyde, dialdehyde, or combinations thereof; and the di-imidoester may be selected from DMA, DMS, DMP, and BS3. In many embodiments, the concentration of protein combined with the dialdehyde/di-imidoester may be less than about 1.0 mg/ml, for example less than about 0.5 mg/ml. The pathogen, in many embodiments, may be selected from a virus, bacterium, fungus, for example a virus selected from coronavirus, influenza, retro, or rhino virus. In some embodiments, the pathogen may be influenza or SARS-COV-2. In many embodiments the dialdehyde/di-imidoester may be one or more of glutaraldehyde, SB3, DMA, DMS, and DMP.

BRIEF DESCRIPTION OF FIGURES

FIG. 5 shows the amino acid sequence of the receptor binding domain of Spike from coronaviruses, SARS-COV-2 and SARS-COV, wherein *—residues within RBD of SARS-COV-2 interact with receptor ACE2. *K (red, K417) was mutated to R417 in our vaccine (top; SEQ ID NO:1). Sequence of RBD sequence (330-524) from Spike protein of SARS-COV-2 (bottom; SEQ ID NO:2).

DETAILED DESCRIPTION

Figure 1:
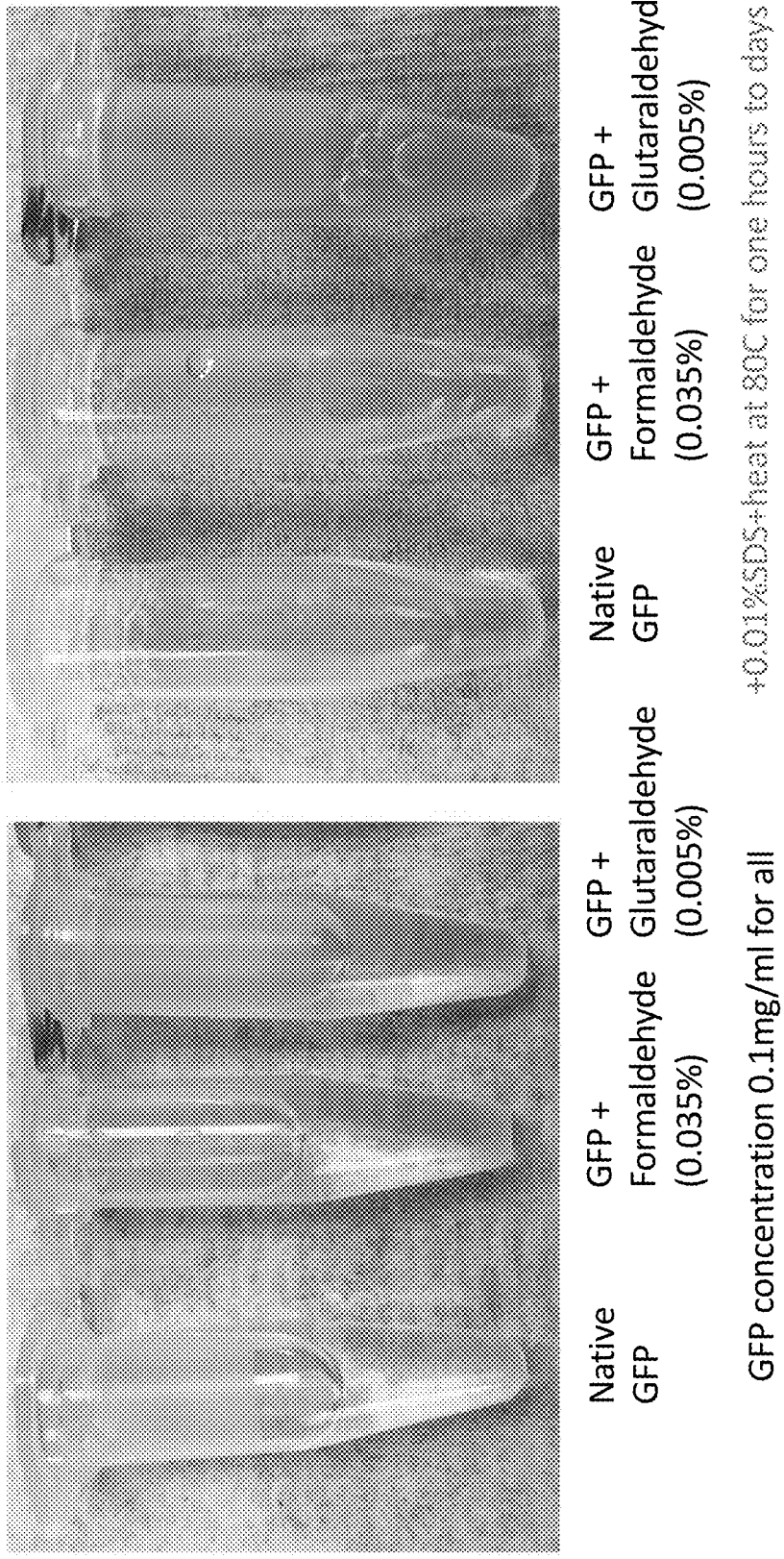
FIG. 1 shows how one embodiment of the present disclosure may be used to generate stable antigens through cross-linking by Glutaraldehyde or Bis sulfosuccinimidyl suberate (BS3), other cross-linking agents, and combinations thereof.

The disclosed methods and compositions are useful in production of universal and long-lasting vaccines against various pathogens, including viruses, fungi, bacteria, etc. In some embodiments, the disclosed method and compositions may be useful in preparing vaccines with neutralizing ability against a broad spectrum of viruses including coronaviruses such as SARS-CoV-2, influenza, rhinovirus, parainfluenza viruses, Metapneumovirus, Respiratory syncytial virus, retroviruses, Hepatitis C, HIV, and other viruses. In many embodiments, the disclosed methods and compositions are useful in creating influenza vaccines with activity against divergent strains. In many embodiments, the disclosed methods and compositions are useful in creating coronaviruses vaccines including SARS-CoV-2 (the causative agent in COVID-19) with activity against divergent strains. The disclosed methods and compositions are also useful in creating monoclonal antibodies, for example against native forms of various antigens, for example proteins.

Introduction

Influenza epidemics have caused disasters in human beings from records in recent two centuries. The 1918 epidemic has caused infections in about 500 million people and has caused ~50-100 million deaths world-wide. In the U.S. prevernal influenza vaccines cost about 2.5 to about 3.0 billion dollar per year, and are expected to reach about 5 billion in 2025. However, due to the limitation of these vaccines, they are only ~50% effective. In this regard, direct medical expenses for treatment of infected patients in USA can reach about 10.4 billion dollar per year, and about 87 billion dollars in indirect costs per year. Worldwide cost could be as high as 10 times these values. There is an urgent need in developing a universal and long-lasting influenza vaccine, as well as vaccines directed to other pathogens.

A major challenge is that rapid changes in influenza viruses make it hard to find a common antigen (one that can be used for a broad spectrum vaccine) among different strains of influenza viruses. For example, the influenza A strain has 18 H subtypes combined 11 N subtypes with total of 18×11 different combinations. While even specific combinations, such as H1N1, change (or mutate) rapidly over time and location. Influenza B has similar issues, though not as many as influenza A. It is very well characterized that A and B strains are main pathogens that cause epidemic in human being every year.

The use of modern RNA- and DNA-sequencing technologies have resulted in a large number of viruses, including both influenza A strain and influenza B strain, being sequenced. Based on sequence comparisons, some portion of the antigens on these viruses are quite conserved and change slowly over time. For examples, Dr. Peter Palese's group found that a fragment from a hemagglutintin subunit 2 protein (HA20) that is conserved among most common influenza viruses, and a vaccine based on this fragment (a synthetic peptide) could trigger production of broadly neutralizing antibodies and protection in mice against influenza viruses of the structurally divergent subtypes H3N2, H1N1, and H5N1 (Taia T. Wang, et al., PNAS, 2010). In some cases, broadly neutralizing antibodies were found from some patients, such as nAB 12D1. These results suggest that there are both theoretical and actual basis to develop a universal and long-lasting influenza vaccine. However, at least two issues remain: 1) how to efficiently discover and select the common antigens and 2) how to present these common antigens to hosts (mammals, including human beings, cattle, pigs, birds, etc.).

The most traditional approach in preparing vaccines is to use killed viruses (dead viruses). This method should, in theory, preserve all the virus's antigens including both B cell antigens and T cell antigens. A second method, using attenuated viruses as vaccine, should also preserve B and T cell antigens. And a third method, using proteins or peptide expressed on the surface of viruses as antigens. Theoretically, when a subject is infected by a virus, the subject should be exposed to, and develop immunity to, all the virus's antigens. Interestingly, in all three methods result in protection (for subsequent challenges) that is incomplete. Specifically, they do not lead to production of broadly neutralizing antibody production, in other words, not all B cell and T cell antigens have been selected due to the instability of these antigens.

Dendritic cells, B-cells, and macrophages are termed antigen-presenting cells (APCs). Immunoglobulin G (IgG) family of proteins is the main player for broadly neutralizing antibody family. Without wishing to be limited by theory, production of IgG needs coordination of T cell, B cells, and follicular dendritic cells (FDCs). Dendritic cells (DC) first present antigens (peptides digested within DC cell from viruses) to naïve T cell in T cell zone, which will move to B cell zone become follicular T cells (Tfh). Follicular T helper cell (CD4 cells) interact with GC B cells presenting antigens from viruses trigger Tfh cell produce IL-21, which will stimulating GC B cell for class switching. At the same time, if there is a FDCs cell presenting native form of antigens (proteins from viruses), high affinity IgG B cells (through membrane bound IgG) interacts with FDCs, which trigger the B cells to convert to Plasma cells and Memory B Cells. During the process, T cells, which is specific to recognize antigens presented by Dendritic cells to help B cell maturation in the germinal center, will become memory T cells for long term protection. To generate broadly neutralizing antibodies (produced by pathogen-specific B cells) as well as pathogen-specific T cells, it is essential for FDCs to present the native form of antigens to the activating B cells (by Tfh) in the germinal center.

Several factors may hamper production of effect vaccines or inhibit native viruses from inducing production of broadly neutralizing antibodies as well as pathogen specific T cells. First, due to the high mutagenesis rate of influenza viruses, many common viral antigens may be buried or are not easily accessible to B cells in GC. Second, due to the instability of protein antigens (protein antigens are unstable either in vitro or in vivo) in vivo, FDCs may not be able to present native form antigens anymore when needed (antigens have been denatured or digested in vivo). Third, traditional processes for preparing vaccine, especially where formalin or beta-propiolactone is used, denatures the native structure of viral antigens. Overall, it is difficult for FDCs to present the common antigens to B cells for further maturation and production of broadly neutralizing antibodies, it also effects the formation of final protective memory T cells. To overcome this obstacle, Applicants describe a novel method of preparing and presenting stable antigens to FDCs during the period of time of B cells class switching and somatic hypermutation so as to generate long lasting broadly neutralizing IgGs producing plasma B cells, memory B cells, memory T cells to protect human beings against future infections of the similar types of pathogens.

Cross-Linking Agent

Various cross-linking agents are useful in performing the disclosed methods, and forming part of the disclosed compositions. In many embodiments, the cross-linking agent may possess a reactive moiety at one or both ends of a molecular chain structure. In many embodiments, the chain structure maybe 4 or more carbon atoms, for example 4, 5, 6, 7, 8, 9, 10, or more carbons, which may be linear, branched, ringed, with one or more double bonds. In some embodiments, the reactive moiety may be a reactive carbon, for example a carboxyl group. In many embodiments, the cross-lining agent may be selected from one or more of an aldehyde, an imidoester, and combinations thereof. In many embodiments, the cross-lining agent may be selected from one or more of a dialdehyde, a di-imidoester, and combinations thereof. In many embodiments, the cross-linking agent may be one or more of glutaraldehyde, adipimidic acid dimethyl ester (DMA), dimethyl suberimidate (DMS), dimethyl pimelimidate (DMP), and bis(sulfosuccinimidyl) suberate (BS3).

Many available cross-linking agents target free amino groups on proteins, for example lysine residues. However, lysine residues may, in some cases, participate host and pathogen recognition. In some embodiments, the disclosed methods of creating a vaccine may include producing a recombinant target antigen lacking one or more lysine residues, or example lysine residues that are accessible to cross-linking agents and/or useful for host or pathogen recognition. In many embodiments, this may aid in avoiding loss of epitopes after cross-linking. In one aspect, recombinant target proteins from an infectious agent (i.e. a virus, bacterium, microbe, etc.) may be created. In these embodiments, the various residues in the wild-type protein may undergo intentional replacement, for example at one or more lysine residues, which may be replaced with arginine. These recombinant proteins may produce an antigen as was performed on RBD of SARS-COV-2, discussed below.

To address the problems discussed above, Applicants have developed methods and compositions for introduction of a cross-linker agent, glutaraldehyde, that maintains the native structure of viral antigenic sites. As shown below, Glutaraldehyde is a 5 carbon linear molecule with terminal reactive oxygen molecules. Glutaraldehyde links sidechains of lysine residues from different parts (even different domains) of the protein. In some embodiments, longer chain aldehydes may be used in the present methods and compositions.

$$O=\overset{1}{\underset{}{}}\overset{2}{\underset{3}{}}\overset{4}{\underset{5}{}}=O$$

Glutaraldehyde

Cross-Linking Compositions

Various concentrations of cross-linker and of protein may be combined in the disclosed compositions for use with the disclosed methods. In most embodiments, the protein concentration may be less than 0.1 mg/ml, and the cross-lining agent may be less than about 0.05 or less than about 5 mM. In many embodiments, the protein concentration of the virus may be diluted to less than about 1.0 mg/ml, 0.9 mg/ml, 0.8 mg/ml, 0.7 mg/ml, 0.6 mg/ml, 0.5 mg/ml, 0.4 mg/ml, 0.3 mg/ml, 0.2 mg/ml, 0.1 mg/ml, 0.09 mg/ml, 0.08 mg/ml, 0.07 mg/ml, 0.06 mg/ml, 0.05 mg/ml, 0.04 mg/ml, 0.03 mg/ml, 0.02 mg/ml, 0.01 mg/ml, 0.001 mg/ml, 0.0001 mg/ml and greater than about 0.00001 mg/ml, 0.0001 mg/ml, 0.001 mg/ml, 0.009 mg/ml, 0.01 mg/ml, 0.02 mg/ml, 0.03 mg/ml, 0.04 mg/ml, 0.05 mg/ml, 0.06 mg/ml, 0.07 mg/ml, 0.08 mg/ml, 0.09 mg/ml, 0.1 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, or 1.0 mg/ml. Where the agent being crosslinked is a virus particle or microbe, the concentration of the target, e.g. virus or microbe, is measured by the protein concentration of the target. Applicants have surprisingly discovered that use of cross-linking agents at very low concentrations may be useful in stabilizing three-dimensional protein structure, which may aid in producing vaccines against a wide range of epitopes that are likely to be encountered in the native protein. In many embodiments, the cross-linking agent may be at greater than about 0.00001%, 0.0001%, 0.0005%, 0.001%, 0.002%, 0.003%, 0.004%, 0.005%, 0.006%, 0.007%, 0.008%, 0.009%, 0.01%, 0.02%, 0.03%, 0.04%, 0.05%, 0.06%, 0.07%, 0.08%, 0.09%, or 0.1%, and less than about 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, 0.0001%. In many embodiments, the cross-linking agent may be at greater than about 0.005 mM, 0.006 mM, 0.007 mM, 0.008 mM, 0.009 mM, 0.01 mM, 0.015 mM, 0.020 mM, 0.025 mM, 0.030 mM, 0.035 mM, 0.040 mM, 0.045 mM, 0.050 mM, 0.055 mM, 0.060 mM, 0.065 mM, 0.070 mM, 0.075 mM, 0.08 mM, 0.085 mM, 0.09 mM, 0.095 mM, 0.1 mM, 0.2 mM, 0.3 mM, 0.4 mM, 0.5 mM, 0.6 mM, 0.7 mM, 0.8 mM, or 0.9 mM, and less than about 1 mM, 0.9 mM, 0.8 mM, 0.7 mM, 0.6 mM, 0.5 mM, 0.4 mM, 0.3 mM, 0.2 mM, 0.1 mM, 0.09 mM, 0.08 mM, 0.07 mM, 0.06 mM, 0.05 mM, 0.04 mM, 0.03 mM, 0.02 mM, 0.01 mM, 0.009 mM, 0.008 mM, 0.007 mM, 0.006 mM, or 0.005 mM.

In embodiments where glutaraldehyde is the cross-linking agent, concentrations of glutaraldehyde of 2% or higher, which may be useful as a high-level disinfectant, may cause precipitant of vaccine samples due to inter-virus cross-linking but not intra-molecule cross-linking and are, in most cases, avoided with the present methods. In most embodiments, the cross-linking concentration of glutaraldehyde is around 0.005% (~0.5 mM). These low concentrations of glutaraldehyde may be insufficient to kill (inactivate) viruses and/or other pathogens. Thus, in some embodiments, after a low initial concentration of Glutaraldehyde treatment for 24 to 48 hours at 4 degree C., formaldehyde or Beta-propiolactone may be added, for example at a concentration of about of 2%. This additional step may aid in eliminating or greatly reducing the number of live viruses after about 24 to about 48 hours at 4 degrees, for example greater than 8 h, 9 h, 10 h, 11 h, 12 h, 13 h, 14 h, 15 h, 16 h, 17 h, 18 h, 19 h, 20 h, 21 h, 22 h, 23 h, 24 h, 25 h, 27 h, 28 h, 29 h, 30 h, 30 h, 40 h, or 45 hr, and less than about 50 h, 45 h, 40 h, 35 h, 34 h, 33 h, 32 h, 31 h, 30 h, 29 h, 28 h, 27 h, 26 h, 25 h, 24 h, 23 h, 22 h, 21 h, 20 h, 19 h, 18 h, 17 h, 16 h, 15 h, 14 h, 13 h, 12 h, 11 h, 10 h, or 9 h. Alternatively, the cross-linked viruses could be completely killed through gamma radiation after cross-linking (Reid 1998).

The virus may be incubated in the cross-linking agent (in some embodiments, glutaraldehyde) solution at about 4° C. for about 24 or 48 hours and additional 2% Formaldehyde or beta-propiolactone treatment another 24 to 48 hours. After about 48 or 72 hours a 10× molar amount of glycine (to ensure residual Formaldehyde is inactivated) is added to the solution, and left for about for 2 hours, to quench the remaining glutaraldehyde and formaldehyde or beta-propiolactone. Cross-linked dead viruses are then concentrated. In some embodiments, the incubation temperature may be less than around 20° C., 19° C., 18° C., 17° C., 16° C., 15° C., 14° C., 13° C., 12° C., 11° C., 10° C., 9° C., 8° C., 7° C., 6° C., 5° C., 4° C., 3° C., or 2° C., and greater than about 1° C., 2° C., 3° C., 4° C., 5° C., 6° C., 7° C., 8° C., 9° C., 10° C., 11° C., 12° C., 13° C., 14° C., 15° C., 16° C., 17° C., or 18° C. In many embodiments, the incubation time may be greater that about 30 min, 40 min, 50 min, 60 min, 70 min, 80 min, 90 min, 100 min, 110 min, 120 min, 130 min, 140 min, 150 min, 160 min, 170 min, 180 min, 4 hrs, 5 hrs, 6 hrs, 7 hrs, 8 hrs, 9 hrs, 10 hrs, 11 hrs, 12 hrs, 15 hrs, 18 hrs, 20 hrs, or 24 hrs, and less than about 72 hrs, 48 hrs, 24 hrs, 20 hrs, 18 hrs, 15 hrs, 12 hrs, 11 hrs, 10 hrs, 9 hrs, 8 hrs, 7 hrs, 6 hrs, 5 hrs, 4 hrs, 3 hrs, 2.5 hrs, 130 min, 120 min, 110 min, 100 min, 90 min, 80 min, 70 min, 60 min, 50 min, 40 min, or 30 min.

Inactivation

Various live agents maybe cross-linked with the disclosed methods and compositions. In some embodiments the killing agent may be a molecule or compound, for example formaldehyde or beta-propiolactone, or any compound able to inactive the agent that does not de-activate the cross-link and or disrupt the three-dimensional structure of the cross-linked antigens. In some embodiments, the agent may be subjected to de-activation by irradiation, for example gamma irradiation.

EXAMPLES

Example 1—Generation of Stable Protein Antigens from Denature at Hush Conditions Applicants have analyzed and elucidated many fundamental mechanisms underlying protein folding and unfolding. It was found that disruption of hydrogen bonds is a driving force in disrupting the 3D structure of protein (Chao Wang et al., ACTA Crystallogr D Strucr Biol, 2014). Later, it was discovered that hydrogen bonds are a primary driving force of protein ab-initio folding (Schuyler Lee et al., Acta Crystallogr D Strucr Biol, 2017). However, the 3D structure of proteins is mostly held by weak hydrophobic interaction (Van der Waals force). These findings indicate that the three-dimensional structure of proteins is fragile and therefore vulnerable to environmental changes. Small perturbations in the environment of proteins could lead to denaturation of the proteins 3D structure. Formalin (formaldehyde), beta propiolactone (BPL), extreme pHs, some solution compositions, vaccine adjuvants (Alu), etc. all cause denaturation of proteins' native three-dimensional structures. To protect the fragile 3D structures of proteins, others have tried to introduce internal disulfide bond (bridges) to help maintain the protein's native structure. However, disulfide bridges can be disrupted by reducing environments in vivo. Another popular cross-linking agent used to maintain protein structures is formalin/formaldehyde. However, formaldehyde can still cause dramatic denaturation of antigens. Furthermore, because of formaldehyde's small size, its ability to support cross-linking is limited to amino acid residues that are located very close to each other, which may not prevent denaturation of the entire protein molecule.

To address the problems discussed above, Applicants have developed methods and compositions for introduction of a cross-linker agent, glutaraldehyde, that maintains the native structure of viral antigenic sites. As shown below, Glutaraldehyde is a 5 carbon linear molecule with terminal reactive oxygen molecules. Glutaraldehyde links sidechains of lysine residues from different parts (even different domains) of a protein. In some embodiments, longer chain aldehydes may be used in the present methods and compositions, for example aldehydes having 6, 7, 8, 9, or 10 carbons.

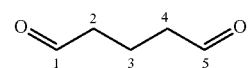

Glutaraldehyde

To test the efficiency of this agent, Applicants employed green fluorescent protein (GFP) as a test model. Specifically, 0.1 mg/ml GFP was added to a 0.005% glutaraldehyde solution (~0.5 mM) in 50 mM HEPES buffer with 50 mM sodium chloride (Applicants note that protein should be dilute into the 0.005% glutaraldehyde solution (~0.5 mM) to avoid precipitation of the protein, when glutaraldehyde is added directly to a solution of protein), pH7.2 (physiological pH is best for stability of target proteins or antigens), for 24 hours at room temperature. In some embodiments, the protein/glutaraldehyde solution may be shaken and/or stirred, in other embodiments it is not shaken, stirred, or mixed. The reaction may be terminated by adding an excess of the amino acid glycine, for example in a molar ratio of about 10:1 glycine:glutaraldehyde, for 10 hours or longer. The prepared GFP sample was then tested for stability in 0.01% SDS at 80° C. for about 1 to 24 hrs. or longer. Native GFP, without glutaraldehyde treatment, will lose its structure and its ability to fluorescence in 0.01% SDS at 80° C. after only 30 min (FIG. 1). However, glutaraldehyde treatment was able to maintain GFP's fluorescence in SDS at high temperature for very long period of time (several weeks or longer) (FIG. 1). These results suggest that glutaraldehyde is an effective agent in maintaining the native structure of proteins in harsh, denaturing environments.

Interestingly, it is traditionally believed that formalin (formaldehyde) also has cross-linking abilities, and, therefore, may be able to protect proteins from denaturation. To investigate, formaldehyde was used to treat GFP protein under the conditions described above. Surprisingly, formaldehyde was unable to stabilize the native form GFP in these conditions, and the fluorescence of GFP was lost after about 30 min in 0.01% SDS at 80° C. (FIG. 1). Thus, formaldehyde would not be an affective agent to protect native proteins from denaturation in harsh conditions.

Example 2—Generation of Influenza a Strain Vaccine with Stable Antigens

Next, Applicants investigated the ability of viruses treated with glutaraldehyde to produce stable antigens. Influenza H1N1 virus was obtained from Charles River company (product ID: 10100374, Influenza A/PR/8/34). Live virus was prepared by diluting to about 0.1 mg/ml into 50 mM pH7.2 HEPES buffer and 50 mM sodium chloride with 0.005% Glutaraldehyde (0.5 mM). In some embodiments, the protein concentration may be less than 0.1 mg/ml, and the glutaraldehyde may be less or more than about 0.05% (5 mM). In many embodiments, the protein may be diluted to less than about 1.0 mg/ml, 0.9 mg/ml, 0.8 mg/ml, 0.7 mg/ml, 0.6 mg/ml, 0.5 mg/ml, 0.4 mg/ml, 0.3 mg/ml, 0.2 mg/ml, 0.1 mg/ml, 0.09 mg/ml, 0.08 mg/ml, 0.07 mg/ml, 0.06 mg/ml, 0.05 mg/ml, 0.04 mg/ml, 0.03 mg/ml, 0.02 mg/ml, 0.01 mg/ml, 0.001 mg/ml, 0.0001 mg/ml and greater than about 0.00001 mg/ml, 0.0001 mg/ml, 0.001 mg/ml, 0.009 mg/ml, 0.01 mg/ml, 0.02 mg/ml, 0.03 mg/ml, 0.04 mg/ml, 0.05 mg/ml, 0.06 mg/ml, 0.07 mg/ml, 0.08 mg/ml, 0.09 mg/ml, 0.1 mg/ml, 0.2 mg/ml, 0.3 mg/ml, 0.4 mg/ml, 0.5 mg/ml, 0.6 mg/ml, 0.7 mg/ml, 0.8 mg/ml, or 0.9 mg/ml. In many embodiments, the glutaraldehyde may be at greater than about 0.00001%, 0.0001%, 0.0005%, 0.001%, 0.002%, 0.003%, 0.004%, 0.005%, 0.006%, 0.007%, 0.008%, 0.009%, 0.01%, 0.02%, 0.03%, 0.04%, 0.05%, 0.06%, 0.07%, 0.08%, 0.09%, or 0.1%, and less than about 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, 0.0001%. Applicants note that 2-5% glutaraldehyde is commonly used as a high-level disinfectant, which could cause precipitant of vaccine samples. The cross-linking concentration of glutaraldehyde used is around 0.005% (~0.5 mM), which, in some cases, may not be enough to kill viruses and/or other pathogens. Thus, in some embodiments, after a low initial concentration of Glutaraldehyde treatment for 24 to 48 hours at 4 degree Celsius, formaldehyde or Beta-propiolactone may be added, for example at a concentration of about of 2%. This may aid in eliminating or greatly reducing the number of live viruses after about 24 to about 48 hours at 4 degrees, for example greater than 8 h, 9 h, 10 h, 11 h, 12 h, 13 h, 14 h, 15 h, 16 h, 17 h, 18 h, 19 h, 20 h, 21 h, 22 h, 23 h, 24 h, 25 h, 27 h, 28 h, 29 h, 30 h, 30 h, 40 h, or 45 hr, and less than about 50 h, 45 h, 40 h, 35 h, 34 h, 33 h, 32 h, 31 h, 30 h, 29 h, 28 h, 27 h, 26 h, 25 h, 24 h, 23 h, 22 h, 21 h, 20 h, 19 h, 18 h, 17 h, 16 h, 15 h, 14 h, 13 h, 12 h, 11 h, 10 h, or 9 h. Alternatively, the cross-linked viruses could be completely killed through gamma radiation (Reid 1998).

The virus is incubated in the glutaraldehyde solution at about 4° C. for about 24 or 48 hours and additional 2% Formaldehyde or beta-propiolactone treatment another 24 to 48 hours. After about 48 or 72 hours a 10× molar amount of glycine (at high concentration to avoid dilution of more than about 10%) is added to the solution, and left for about for 2 hours, to quench the remaining glutaraldehyde and formaldehyde or beta-propiolactone. Cross-linked dead viruses are then centrifuged.

Glutaraldehyde treated virus was then mixed with Alum Adjuvants including one or more of the following: amorphous aluminum hydroxyphosphate sulfate (AAHS), aluminum hydroxide, aluminum phosphate, potassium aluminum sulfate (Alum) as defined and referred by CDC (Center of Disease Control, USA), obtained from Millipore Sigma (Product ID: 239186-Aluminum hydroxide or 255963-Aluminum phosphate, most of time), or Freund Incomplete adjuvant, or Freund complete adjuvant. Other pharmaceutically acceptable adjuvants are known in the art. Mice were injected with ~10 ug of Glutaraldehyde treated virus+adjuvant sample in 100 ul. A second injection was performed two weeks after the first, and third injection four weeks after the first.

Serum was collected from each mouse about two months after first immunization. Serum was sent to VIRAPUR (San Diego, USA) for testing, who conducted hemagglutination inhibition (HAI) analysis.

Figure 2:
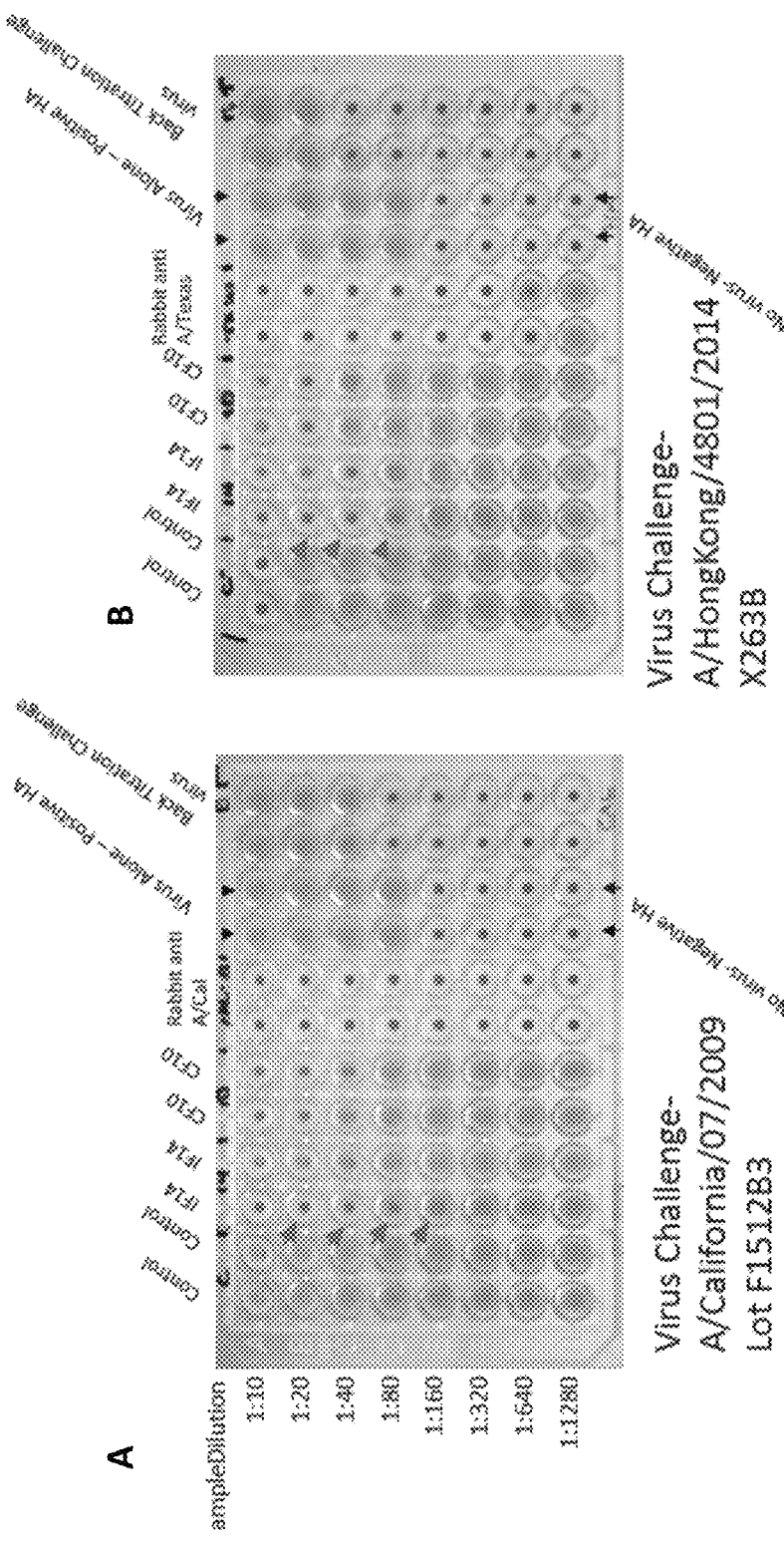
FIG. 2 shows one embodiment of the present disclosure providing broad protections against the two new viruses are gained after immunization with vaccine prepared from Influenza A/PR/8/34 after two months from first time immunization. IF14: serum obtained from mice immunized with vaccine containing Alum adjuvant, aluminum sulfate mixed with sodium or potassium hydroxide plus a variable amount of phosphate, and final boosting (which may be a third time) after 30 days. CF10: serum obtained from mice immunized with vaccine containing Alum Adjuvant and final boosting (third time) after 10 days.

Two month (9 weeks) Serum HAI assay—Serum was also collected from mice immunized at 10 days and 4 weeks (~30 days) post injection. Here, samples were collected at 60 days post injections (30 days after third immunization). Samples were again sent to VIRAPUR for HAI assays. FIG. 2 shows that this serum resulted in inhibitory activity after about 80 to 160× dilution (much greater than 40× dilution). Specifically, about 80-160× against H1N1 (A/California/07/2009) (FIG. 2A) and 80× dilution against H3N2 (A/HongKong/4801/2014) (FIG. 2B). Interestingly, the traditional viruses killing approach by formaldehyde does not generate any HAI activities (see controls in FIGS. 2A and 2B). These results suggested that the presently disclosed compositions and methods could produce an effective vaccine from a 1934 Puerto Rico H1N1 virus that could effectively neutralize an H1N1 virus from a 2009 California strain (effective after ~80-160 times dilution), as well as neutralize an H3N2 virus from a 2014 Hong Kong strain (effective after ~80 times dilution). Thus, the disclosed methods and compositions are effective at creating vaccines with broad effectiveness against a variety of viruses from different places, different times, and even different subtypes. That is, the disclosed methods and compositions are useful in producing a universal and long-lasting vaccine.

Example 3—Generation of Influenza B Strain Vaccine with Stable Antigens

A similar approach was used to prepare a B strain vaccine. In addition, a vaccine was produced using traditional methods (i.e. using formaldehyde to kill virus and prepare the vaccine). The B strain virus was again obtained from Charles River company (product ID: 10100379, B/Lee/40).

Two batches of virus, an A Batch and B Batch, were prepared as follows. A batch: Purified live viruses were diluted to about 0.1 mg/ml in 50 mM HEPES and 50 mM NaCl buffer (pH7.2) with 0.005% Glutaraldehyde. The glutaraldehyde/virus mixture was incubated at 4° C. for about 24-48 hours. Formaldehyde or beta-propiolactone was added to the solution with 2% final concentration and incubated another about 24 to 48 hours. After which a 10× molar excess of glycine was added to quench the remaining glutaraldehyde and formaldehyde or beta-propiolactone, and the mixture was incubated an additional 2 hours. B batch: Purified live viruses are diluted to 0.1 mg/ml (total of 10 ml) 50 mM pH7.2 HEPES buffer with 2% formaldehyde, incubated at 37° C. for 24 hours, and again quenched by addition of a 10× molar excess of glycine, with further incubation for 2 hours.

Both batches of viruses were concentrated. The treated viruses were mixed with or without Alum Adjuvants. 100 ug of sample was injected to each mice each time. After first injection, second injection two weeks later, and third injection four weeks or one month later. Serum is collected about two months after the first injection. Four groups of mice were immunized as described:

Group 1: viruses treated with formaldehyde plus adjuvants (total of 5 mice).
Group 2: viruses treated with formaldehyde without adjuvants (total of 4 mice).
Group 3: viruses treated with glutaraldehyde plus adjuvants (total of 6 mice).
Group 4: viruses treated with glutaraldehyde without adjuvants (total of 4 mice).

Figure 3:
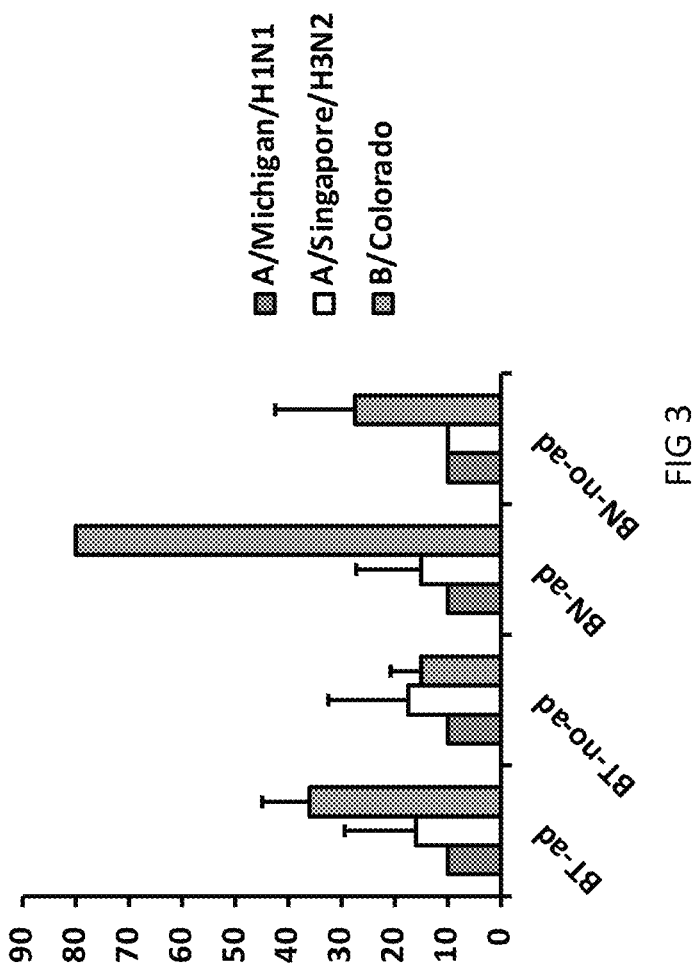
FIG. 3 shows an aspect of the present disclosure providing broad protection against B/Colorado/2017 is gained after immunization with vaccine prepared from influenza B/Lee/40 after two months from first time immunization or one month after the third time immunization. Y-axis, serum dilution folds. For example, 40 means after 40 times dilution of the original serum for the experiment.

Serum was collected and subjected to HAI assays (FIG. 3). As shown in FIG. 3, vaccine prepared from B strain virus has no protection on A strain virus either H1N1 (A/Michigan/H1N1) or H3N2 (A/Singapore/H3N2) (red and yellow, FIG. 3, HAI<<10). However, traditional preparation of B strain vaccine produced with formaldehyde (Group 1) injected with adjuvant did generate a weak protection against a different B strain (B/Colorado/2017) but with an HAI score less than 40 (i.e. less than the standard level 40 times dilution) (BT-ad, FIG. 3). This level of inhibition is borderline for protection. Without adjuvant (Group 2), traditional vaccine performed more poorly (BT-no-ad, FIG. 3, HAI<<20). However, the vaccine prepared with glutaraldehyde plus adjuvant supported inhibition even after 80× times dilution (BN-ad, FIG. 3, HAI>>80). Again, the inhibition dropped when no adjuvant (Group 4) was employed (BN-no-ad, FIG. 3, HAI>20<40).

This data demonstrates that a vaccine prepared as described provides for broad immunity. Specifically, the disclosed methods and compositions were used to produce an influenza B strain vaccine from a 1940 B virus that was able to protect against another B virus from a 2017 Colorado strain. These results again show that the disclosed methods and compositions are useful in producing influenza B strain vaccines that protect against various B strains from different subtypes, obtained at different times and locations to create a universal, long-lasting vaccine.

Potential Application to Other Viruses that are Difficult to Generate Vaccines.

Figure 4:
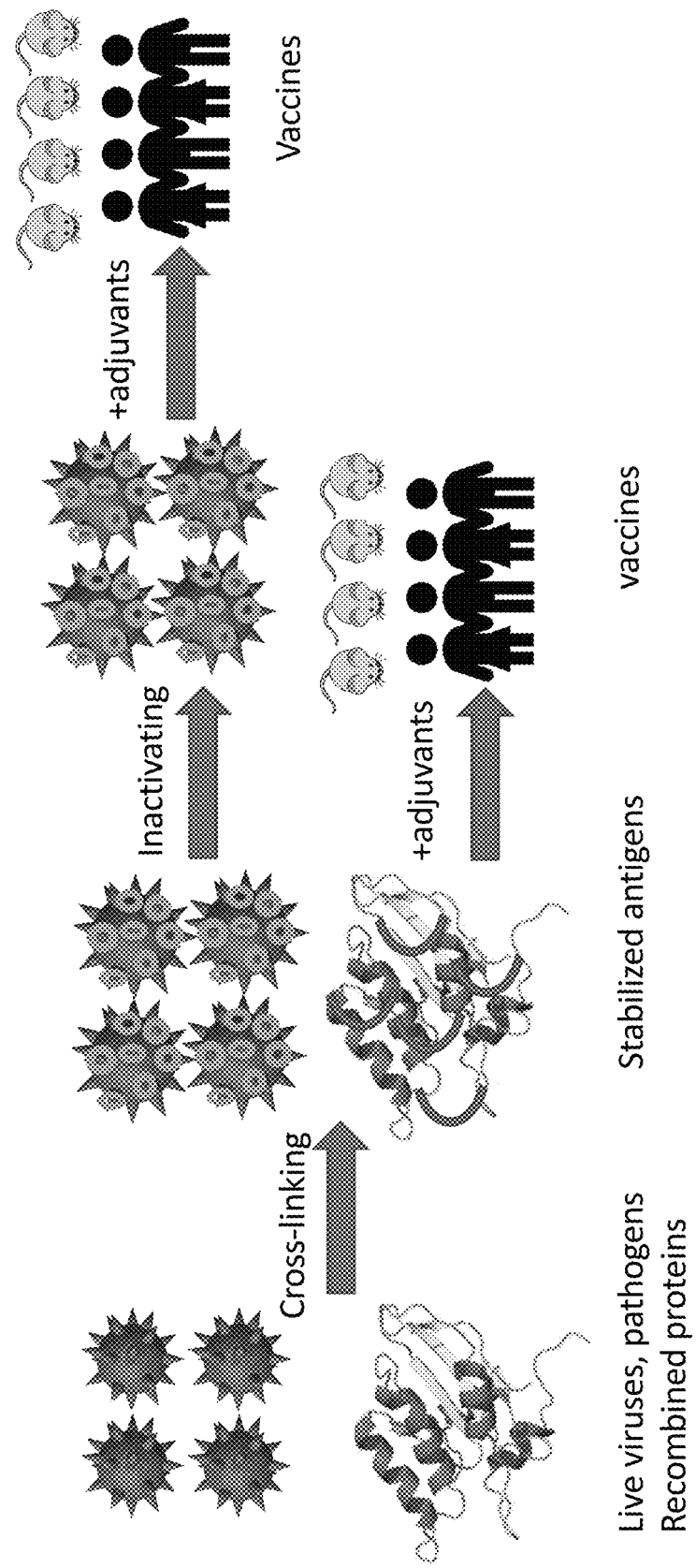
FIG. 4 is a schematic of one embodiment of the present method of creating a vaccine.

As described in the diagram of FIG. 4, the presently disclosed methods and compositions may be used to create universal vaccines effective against a variety of viruses with broad reactivity across variable strains and sub-strains from various locations and times, including influenza, coronaviruses (including SARS-CoV-1, SARS-CoV-2, MER etc.), rhinovirus, retrovirus, parainfluenza viruses, Metapneumovirus, Respiratory syncytial virus, Hepatitis C, HIV, and other viruses. The disclosed methods and compositions may be used to create vaccines against various other pathogens such as bacterial, fungi, parasites etc.

Immunization Method

One embodiment of the disclosed method of immunization is as follows:

Concentrate the treated (i.e. cross-linked and inactivated according to the presently described methods) virus 0.1 mg/ml.
Wash pelleted virus twice with cold PBS
Concentrate the washed virus.
Re-suspend the virus in 200 µl PBS.
Add 200 µl Alum Adjuvant and mix vigorously for 1-2 minutes.
Emulsify the virus/adjuvant mixture in Eppendorf Thermomix at 1400 rpm for 5 hours at room temperature.
Immunize C57bl/6 mice with intraperitoneal injection of 100 µl (10 µg virus) virus/adjuvant. (First immunization).
Two weeks after first immunization, boost the mice with intraperitoneal injection of 100 µl (~10 µg virus) virus/Alum adjuvant prepared in the same way. (Second immunization).
Two weeks later, repeat the boost with intraperitoneal injection of 100 µl (10 µg virus) virus/Alum adjuvant. (Third immunization).
30 days after the third immunization, collect blood from tail. Store the serum at −20° C. for second day delivery, or store at −80° C. for long time storage.

CONCLUSION

It has been a big challenge for people to develop universal and long-lasting vaccines against influenza, HIV, and other viruses. It is known that a universal and long-lasting vaccine should have triggered the production of broadly neutralizing antibodies from hosts while these antibodies are mostly IgG family members, which are usually produced from plasma B cells. Plasma B cells are produced from B cells in germinal center of a lymphoid after class switch and hyper mutation process with the help of follicular dendritic cells (FDCs) and follicular T cells. One step of the process relies on FDCs to present native form of antigens for the entire duration of the process, which may last weeks and months (2 months).

One challenge in the field of immunization is to present native antigens for this long period of time. This is, in part, due to the instability and short-lived nature of native antigens. In this regard, it is found that adjuvants which quickly precipitate antigens may aid in protecting the native three-dimensional structure of the antigens—allowing the antigens to maintain their native structure longer in vivo. This is why traditional vaccines rely on co-administration of adjuvants. However, for influenza, HIV, and other viruses, these traditional methods do not work due to the limited number of common antigens. The limited number of common antigens is, in part, caused by the high mutation rates in many of these viruses. Thus, the ability to preserve the limited number of common antigens within these viruses in their native form, after injection, is useful. This would enhance the time these antigens are available to induce the complicated germinal center B cell maturation process.

Traditional viral inactivation and cross-linking agents, such as formaldehyde or Beta-propiolactone, do not work effectively, nor does the inclusion of artificial disulfide bridges. Instead, Applicants have surprisingly found that cross-linking of antigens with glutaraldehyde provides a more efficient cross-linking that helps preserve the native structure of the antigen. The disclosed method was also able to increase the stability of GFP proteins in denaturing environments, such as SDS and high temperature. These GFP experiments demonstrated that glutaraldehyde is useful in maintaining protein stability, and that GFP is a good system for testing this feature.

Applicants note that use of higher concentrations of glutaraldehyde (for example about ~2% and above) is a common disinfection agent, but unsuitable for creating vaccines as presently described. Specifically, high concentrations of glutaraldehyde cause inter-molecule cross-linking, i.e. aggregation of particles, which results in precipitation of the virus particles or other pathogens. Precipitated viral particles, or precipitated antigens, are poor vaccine candidates at least because they result in fewer candidate epitopes being presented to the subject's immune system and a concomitant loss in epitope complexity. This may also result in a failure to cross-link within protein antigens (intra-molecular cross-linking, which may aid in stabilizing antigen three dimensional structures). Applicants have, surprisingly, found that use of low concentration of glutaraldehyde (~0.005% or ~0.5 mM or less) as well as low concentrations of viruses or proteins (less than 0.1 mg/ml) resolve these issues and allows for creation of a superior vaccine. At the same time, this low concentration of glutaraldehyde (from 0.005% or 0.5 mM to ~0.5% or 50 mM) is unable to kill viruses or other pathogens completely, an additional inactivating step is required to completely kill viruses or pathogens to prepare the vaccine starting from an alive virus or pathogen.

Applicants have shown that the disclosed methods and compositions are effective for producing vaccines from both influenza A strain viruses and B strain viruses. The disclosed methods and compositions are also useful in producing highly effective vaccines from other virus types such as coronaviruses such as SARS-CoV-2, HIV, as well as diverse pathogens such as bacteria and fungi.

Based on the disclosed examples, Applicants derived a general procedure of producing universal and high potent vaccines against all pathogens as shown in FIG. 4.

Example 4—Development of a Potent SARS-COV-2 Vaccine

During the process of developing a universal vaccine against influenza, COVID-19 pandemic (caused by coronavirus, SARS-COV-2) broke out in late 2019 in Wuhan, China and quickly spread to the world in the early 2020. The SARS-CoV-2 virus has now infected hundreds of million people world-wide (COVID-19 patients), resulting in millions of deaths (see worldometers.info/coronavirus). Although several vaccines have been approved including: 1) mRNA of Spike protein from SARS-CoV-2 based, 2) DNA of Spike protein through adenovirus carriers based, 3) inactivated viruses of SARS-CoV-2, and 4) recombinant protein from SARS-COV-2. However, all vaccines mentioned above fail to prevent new infections by newly emerging variants of SARS-CoV-2. New variants are keeping emerging to threaten the life of human beings even after all mentioned vaccines. It is likely that the virus will co-exist with human beings in the future. Thus, there is an urgency to develop a long-lasting vaccine to protect people against SARS-CoV-2 with emerging new variants.

The approaches generating all above approved vaccines have different disadvantages, which may prevent the development of a vaccine with high efficacy, safety, easy handling, convenient delivering, and an affordable price for people all over the world. Specifically, 1) mRNA as vaccine has problems of high price of production, low stability, and strict high requirements of handling (such as low temperature storage for stability), furthermore, the Spike protein is very fragile for denature even it is translated in host, which leads to limited protection from emerging new variants, people need continuing vaccinations (or 'boostings') to gain protections; 2) Adenovirus as carriers could be destroyed in vivo by the immune system of individual who got infected by this virus before since adenoviruses are common cold viruses, majority of population have infection history and have immune memory to destroy new infections; 3) Inactivated viruses also have several disadvantages—first, protein antigens, mostly the Spike protein on the surface of SARS-COV-2 is highly flexible and vulnerable for denature by formaldehyde or Beta-propiolactone and during the procedure, traditional virus killing could lead to loss of native antigen epitopes of the Spike protein. and second, there are reports that inactivated virus vaccines could lead to antibody dependent enhancement (ADE) infection of similar viruses with some slightly different strains, such as that found in dengue viruses; 4) recombinant protein has similar issue of antibody dependent enhancement infection as well as low stability issues. In this regard, we believe that our approaches of cross-linking and inactivating viruses used to generate influenza vaccines described above should be applicable to generate high potent and lasting-vaccines against SARS-CoV-2, which could obtain protections against newly emerging variants of SARS-CoV-2. Due to lack of available live viruses of SARS-CoV-2 for testing of our novel procedure in our current new start-up LLC company conditions, we are starting to explore a novel approach to develop a potent vaccine only based on recombinant protein and to overcome all disadvantages mentioned above. All these disadvantages lead to the escape or breakthrough of SARS-CoV-2 newly emerging variants even after vaccinations with all above approved vaccines against SARS-CoV-2 so far.

The presently disclosed compositions, methods, and technology is universal for developing vaccines against all other viruses or pathogens. However, due to inability to obtain the alive SARS-CoV-2 virus, we are unable to generate dead virus vaccine of SARS-CoV-2, which contains more B cell and T cell antigens and are ideal for long-lasting SARS-CoV-2 vaccine. However, we plan to use a small portion of protein from SARS-CoV-2 to generate a potent vaccine by introducing our novel approach. In this regard, a potent vaccine against SARS-COV-2 has been developed using the receptor binding domain (RBD, residue 330 to residue 524, P0DTC2, bottom FIG. 5) of Spike protein and the entire Spike protein from SARS-COV-2 against the SARS-COV-2. The present vaccine is produced using the cross-linking approach by glutaraldehyde, as discussed above. This approach overcomes the disadvantages described above for all currently developing vaccines for treatment of SARS-COV-2 infections.

Results

As demonstrated above, cross-linking using glutaraldehyde stabilizes antigens and epitopes on antigens so as to keep them at native conformation in vivo for a long time after immunization. The cross-linking process will help the host maintain a long immune response such as to provide for B cell class switch, B cell hyper-mutation affinity maturation, generating long lasting plasma B cells (which typically generate high affinity broadly neutralizing IgG antibodies), memory B cells, and memory T cells, etc. in germinal center. After the long immune response, human hosts will develop immune memory against future infection of the same virus or mutated versions for long time protection.

To create the current vaccine, a K417R-mutated version of RBD was created. This version of RBD remains able to bind to ACE2 after cross-linking with 0.005% (0.5 mM) glutaraldehyde. Based on published structural information between receptor binding domain (RBD, residue 330 to residue 524—FIG. 5 bottom) of Spike protein from SARS-COV-2 and the human host receptor ACE2 (PDB ID: 6MOJ), it was proposed that an antibody that binds to the surface of RBD and blocks the binding of ACE2 would protect a human host, and prevent infection by SARS-COV-2. In this regard, the RBD domain alone or the entire Spike protein were selected as vaccine candidates against SARS-COV-2.

Figure 6:
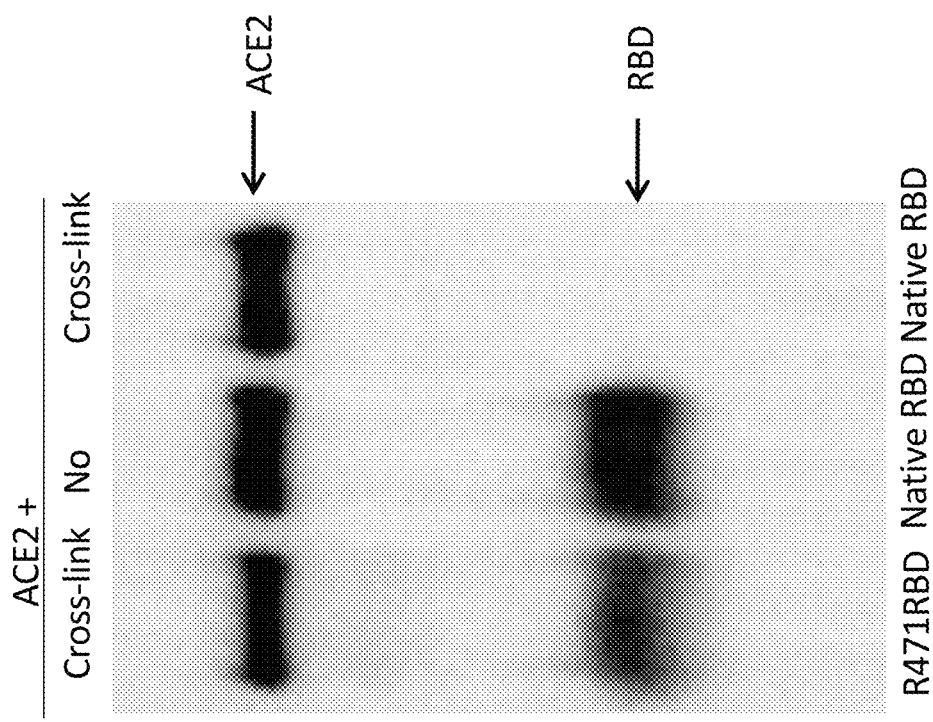
FIG. 6 shows 6His tagged ACE2 pulldown native and cross-linked R417-RBD, but not cross-linked native RBD.

From structural information and sequence alignment (FIG. 5), we found that a lysine residue (K417) is involved in interaction between RBD and ACE2. To avoid reaction of this lysine residue with cross-linked agent, glutaraldehyde, which could lead to the loss of binding of ACE2 after cross-linking, as noted above a lysine to arginine (K417R) mutation version of RBD was created as well as a similarly mutated full-length spike protein. Both proteins were expressed in Hi5 insect cells. Proteins were also expressed in human 293T cells, yeast, and bacteria. Proteins of the mutated version of RBD (K417R) with or without cross-linking could bind to ACE2 in vitro (FIG. 6). However, the native form of RBD, after cross-linking, does not bind to ACE2 anymore (FIG. 6).

Figure 7:
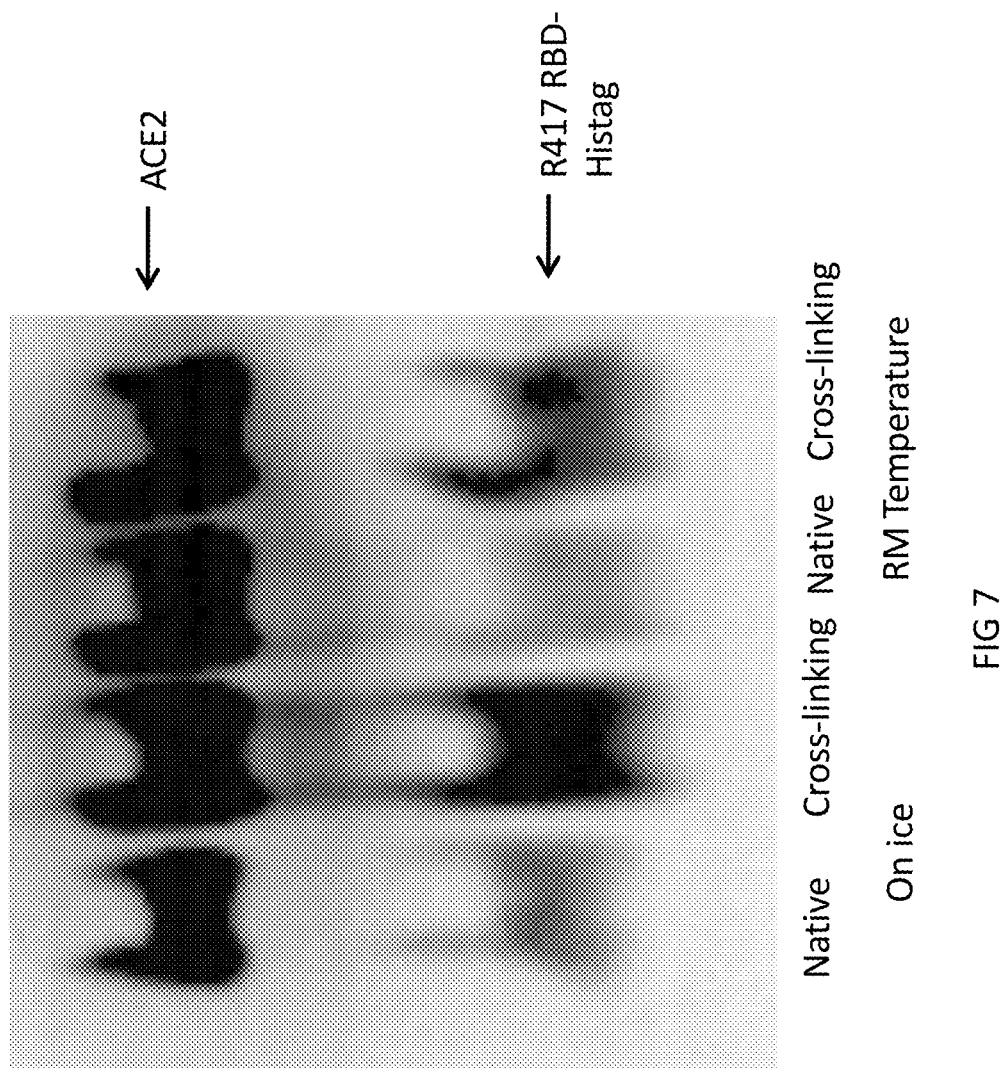
FIG. 7 shows cross-linked R417-RBD 6 His tagged is stable on ice or room temperature for at least one week. Native RBD is unstable without cross-linking.

The cross-linked version of K417R RBD is stable on ice or room temperature for a long time. This was beneficial because stability of vaccine is a big issue, especially when delivering the vaccine to remote area or undeveloped zones all over the world. As demonstrated in FIG. 6, cross-linking of RBD resolves this issue. From our experiments, the cross-linked K417R RBD is stable on ice and room temperature after one week (FIG. 7). However, native form of RBD without cross-linking is degraded after one week (FIG. 7). In some embodiments, cross-linked antigens may be stable from about 0° C. to about 0° C., for extended periods of time, for example from about 1 week to about 10 weeks. In some embodiments, the cross-linked antigens are stable at temperatures greater than about 0° C., 1° C., 2° C., 3° C., 4° C., 5° C., 6° C., 7° C., 8° C., 9° C., 10° C., 11° C., 12° C., 134° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C. or 39° C., and less than about 40° C., 39° C., 38° C., 37° C., 36° C., 35° C., 34° C., 33° C., 32° C., 31° C., 30° C., 29° C., 28° C., 27° C., 26° C., 25° C., 24° C., 23° C., 22° C., 21° C., 20° C., 19° C., 18° C., 17° C., 16° C., 15° C., 14° C., 13° C., 12° C., 11° C., 10° C., 9° C., 8° C., 7° C., 6° C., 5° C., 4° C., 3° C., 2° C., or 1° C. In many embodiments, the disclosed cross-linked antigens are stable for greater than about 1 week, 1.5 weeks, 2 weeks, 2.5 weeks, 3 weeks, 3.5 weeks, 4 weeks, 5 weeks, 6 weeks, 7 weeks, 8 weeks, 9 weeks, 10 weeks, 15 weeks, 20 weeks, 25 weeks, 30 weeks, 35 weeks, 1 year, or more, and less than about 2 years, 1 year, 50 weeks, 40 weeks, 30 weeks, 25 weeks, 20 weeks, 15 weeks, 10 weeks, 9 weeks, 8 weeks, 7 weeks, 6 weeks, 5 weeks, 4 weeks, 3 weeks, 2 weeks, or 1 week.

Figure 8:
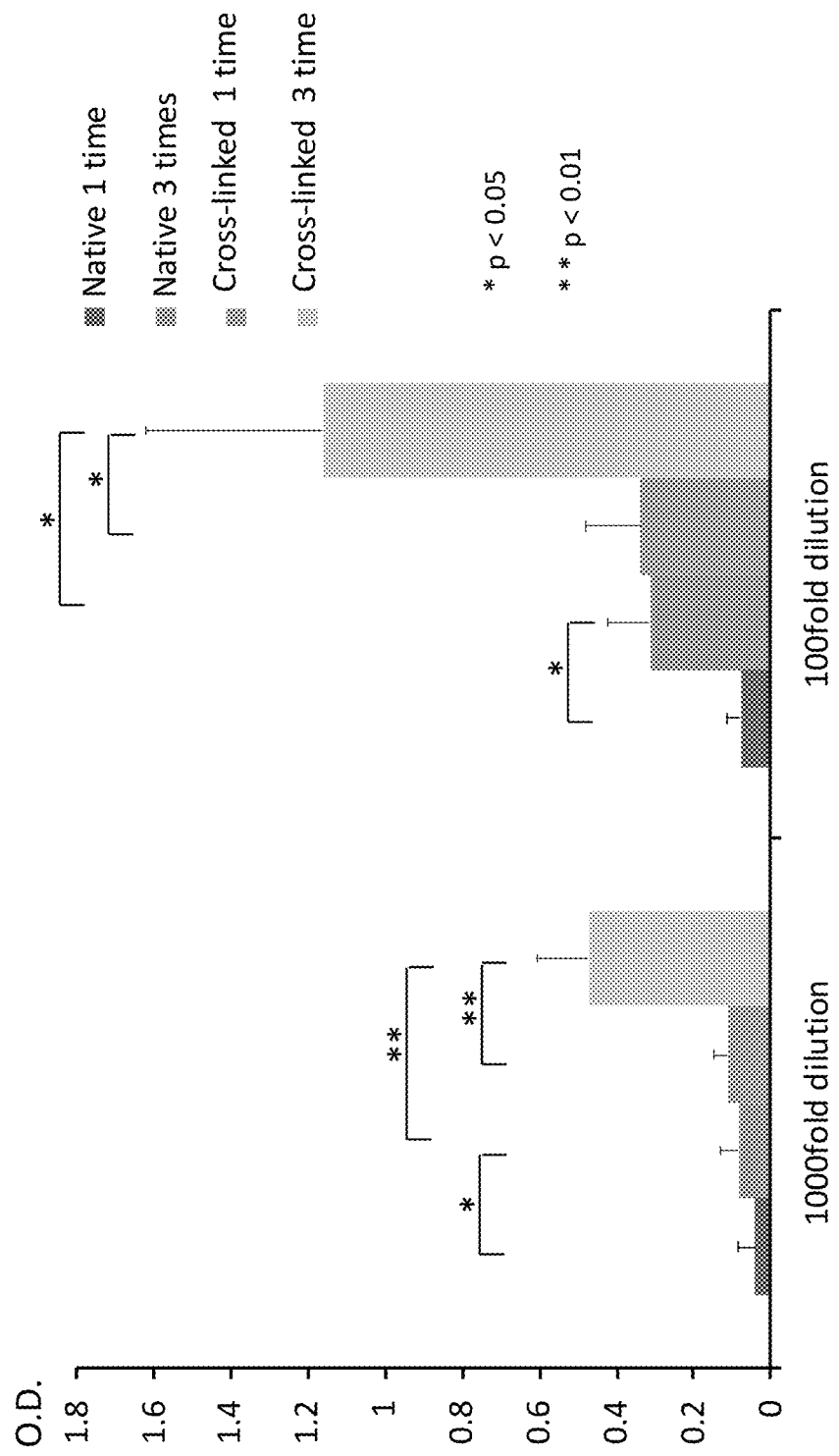
FIG. 8 shows cross-linked RBD-K417R leads to much higher Serum RBD IgG antibody titer Compared to native RBD two months after one or three immunizations. Cross-linking as described herein.
Figure 9:
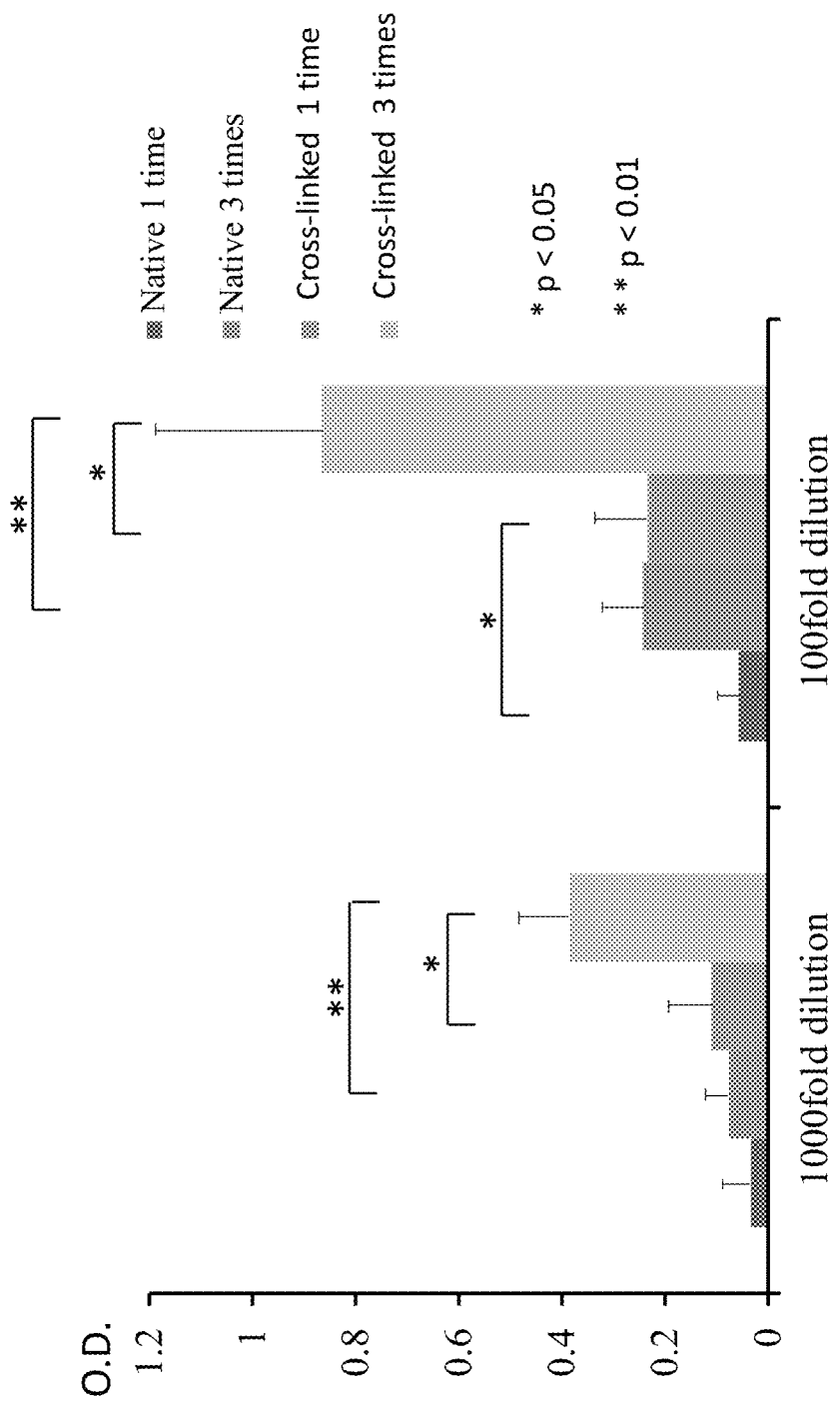
FIG. 9 shows cross-linked RBD-K417R leads to much higher Serum RBD IgG antibody titer Compared to native RBD three months after one or three immunizations.

The cross-linked version of K417R RBD generates a much higher titer (~3 times higher) of IgG molecules in mice, as compared to IgG titers in mice immunized with a native form of RBD. The IgG titers against RBD were determined as described above. The titers are higher (~3 times higher) from that of cross-linked RBD immunized RBD compared to native form of RBD immunization two months after administration with either a one-time immunization or with two additional boosts two weeks apart (a total of three immunizations with ~10 ug of RBD sample each time) in mice respectively (FIG. 8). The higher titers of IgG still remain after three months (FIG. 9). This result demonstrates that cross-linked version of K417R RBD is more effective in triggering an immune response than that of non-cross-linked RBD. In many embodiments, cross-lined antigen may increase IgG titers in subjects compared to non-cross-linked antigens by about 2× to about 100×, for example greater than about 1×, 2×, 5×, 10×, 15×, 20×, 25×, 30×, 40×, 50×, 60×, 70×, 80×, 90×, 100×, 150×, 200× or more, and less than about 1000×, 500×, 200×, 100×, 90×, 80×, 70×, 60×, 50×, 40×, 30×, 20×, 15×, 10×, 9×, 8×, 7×, 6×, 5×, 4×, 3×, or 2×. 40 µg/ml RBD-his was coated on the ELISA plates overnight and blocked by PBS with 30% FBS. Mouse serum was diluted at 100-fold and 1000-fold in the dilution buffer (PBS with 2% FBS) and incubated on the plate for 1 hour at room temperature. The plate was then washed three times. Alkaline phosphatase (AP) conjugated anti-mouse IgG antibody (Sigma A3562) was then added and incubated for 1 hour. The plate was washed five times. AP substrate was added. The absorbance at 405 nM was read at different time points after substrate.

Figure 10:
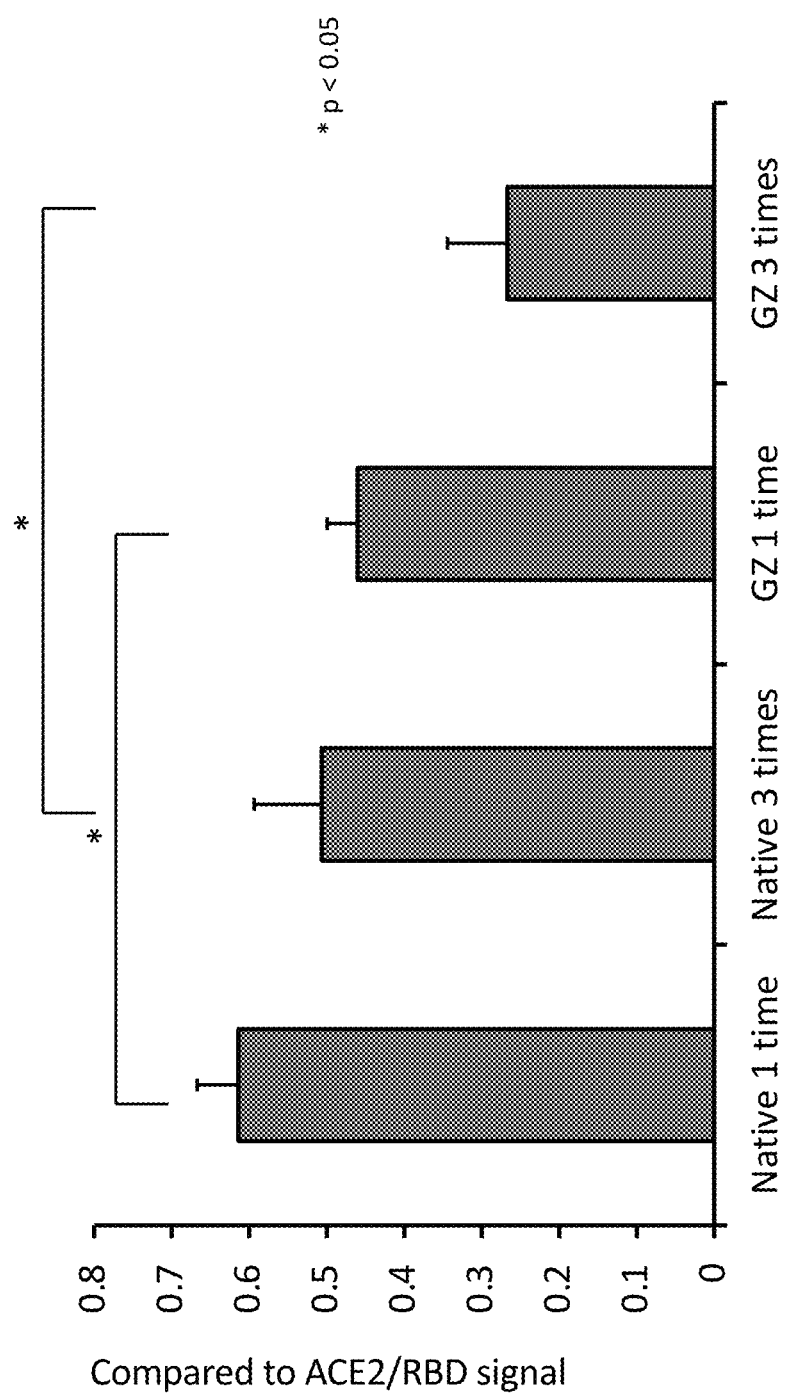
FIG. 10 shows Cross-linked RBD K417R generated much higher Blocking antibodies against ACE2 binding to RBD coated plates at 1000-fold serum dilution ELISA.

The cross-linked version of K417R RBD generates more broadly neutralizing antibodies, which block the binding of ACE2, than that of native form of RBD. We found that the serum from mice after immunized with cross-linked K417R RBD have much higher blocking ability against ACE2 than that of native form of RBD (FIG. 10). 40 µg/ml RBD-tag was coated on the ELISA plates overnight and blocked by PBS with 30% FBS. Dilution buffer alone was also used for signal normalization. Mouse serum was diluted at 1000-fold in the dilution buffer and incubated on the plate for 1 hour at room temperature. The plate was then washed three times. 50 µg/ml ACE2-his was added and incubated for 1 hour at room temperature. The plate was then washed three times. Biotinylated anti-6*histidine tag antibody (Biorad MCA1396B) was then added and incubated for 1 hour at room temperature. The plate was then washed three times. Streptavidin-AP was then added and incubated for 1 hour at room temperature. The plate was washed five times. AP substrate was added. The absorbance at 405 nM was read at different time points after substrate. The data was presented as the ratio of absorbance with mouse serum divided by absorbance with the dilution buffer alone. The final bound ACE2 readouts reflect the blocking degree of antibodies. The less of ACE2 detected (readout) on the ELISA plates, the higher blocking property of the antibodies (FIG. 10).

Various cross-linking agents may be useful in performing the disclosed methods and creating the disclosed vaccines. In some embodiments, the cross-linking agents may aid in covalently attaching to free amines in a protein. In some embodiments, the disclosed agents may link free amines, or other groups from different residues within the protein chosen as antigen.

Other cross-linking agents, such as bis sulfosuccinimidyl suberate (B S3), dimethyl adipimidate (DMA), dimethyl suberimidate (DMS), and dimethyl pimelimidate (DMP), may also be useful. In many aspects, these agents may be used in conjunction with or as an alternative to glutaraldehyde in creating the disclosed vaccines. In other aspects, other agents may be useful, wherein the agent is able to covalently connect/link (i.e. cross-linking) chemical groups within a protein antigen (i.e. intra cross-linking) and stabilize protein antigens. In one embodiment, such a cross-linker is bis sulfosuccinimidyl suberate (BS3) as shown below:

In many embodiments, the disclosed cross-linking agents useful in creating the disclosed antigens and vaccines, may covalently link different parts of a protein while maintaining the protein's three-dimensional structure. BS3, DMA, DMS, and DMP were analyzed for the ability to cross-link RBD, similar to studies described above, these agents were shown to have similar effects in providing RBD antigen with similar stability and effectiveness as compared with glutaraldehyde cross-linking.

Described herein are compositions and methods for creating very potent vaccines against a variety of targets, including SARS-COV-2 and influenza. In many embodiments, the disclosed vaccines may be created using a small region of the target, for example the RBD region of SARS-COV-2. This may dramatically reduce the likelihood of the disclosed vaccines suffering from antibody dependent enhancement, as is seen with other vaccines. Due to the small size of RBD and drastic sequence difference of the RBD region among coronaviruses, Applicant's vaccine overcomes antibody dependent enhancement problems compared to vaccine caused by inactive viruses or the entire Spike protein. Interestingly, two recent reports found that over 90% of broadly neutralizing antibodies from COVID-19 patients or vaccinated individuals are directed against RBD of the Spike protein (Piccoli, Park et al. 2020, Greaney, Loes et al. 2021). These results suggest that the mammalian immune system may also use RBD as the main antigen to generate broadly neutralizing antibodies against SARS-COV-2.

Applicants noticed that most of cross-linking agents work through free amino groups on lysine residues while lysine residues could in participate host and pathogen recognition. To avoid the loss of epitopes after cross-linking, intentional replacement of lysine residue with arginine in individual recombined protein antigen could avoid this issue as we did in RBD of SARS-COV-2.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed description is to be regarded as illustrative in nature and not restrictive.

Applicant claims, in part:

1. A method for prepare a vaccine, the method comprising:
combining a dialdehyde/di-imidoester with a pathogen;
contacting the dialdehyde/di-imidoester with proteins from the pathogen, and allowing the dialdehyde/di-imidoester to form intra-protein bonds to create dialdehyde/di-imidoester-modified pathogen proteins;
removing or reacting dialdehyde/di-imidoester not bonded to protein;
isolating the dialdehyde/di-imidoester-modified pathogen proteins; and
combining the dialdehyde/di-imidoester-modified pathogen proteins with an adjuvant.

2. The method of claim 1, wherein the concentration of protein combined with the dialdehyde/di-imidoester is less than about 1.0 mg/ml.

3. The method of claim 2, wherein the concentration of protein is less than about 0.5 mg/ml.

4. A method of immunizing a subject, the method comprising:
injecting a subject with a dialdehyde/di-imidoester-modified pathogen protein;
injecting the subject a second time with the dialdehyde/di-imidoester-modified pathogen protein.

5. The method of claim 4, wherein the subject is a mammal or avian.

6. The method of claim 5, wherein the subject is selected from a human, a cow, a pig, horse, cat, dog, bird, or chicken.

7. The method of any one of claim 1 to claim 6, wherein the dialdehyde/di-imidoester comprises 4 or more carbons.

8. The method of any one of claim 1 to claim 7, wherein the dialdehyde/di-imidoester comprises a short chain dialdehydes/di-imidoester with 4, 5, 6, 7, 8, 9, or 10 carbons.

9. The method of any one of claim 1 to claim 8, wherein the dialdehyde/di-imidoester is selected from glutaraldehyde, dialdehyde, SB3, DMA, DMS, DMP, or combinations thereof.

10. The method of any one of claim 1 to claim 9, wherein the dialdehyde is glutaraldehyde.

11. The method of any of claim 1 to claim 3, wherein the pathogen is selected from a virus, bacterium, fungus.

12. The method of any of claim 1 to claim 11, wherein the pathogen is a virus selected from coronavirus, influenza, retro, or rhino virus.

13. The method of any one of claim 1 to claim 12, wherein the pathogen is influenza.

14. The method of any one of claim 1 to claim 12, wherein the pathogen is SARS-COV-2.

15. A method of creating a vaccine from a virus, comprising:
contacting the virus with a first dialdehyde/di-imidoester;
incubating the virus and the first dialdehyde/di-imidoester for a first time period, to allow viral proteins to crosslink to form a cross-linked mixture;

treating the mixture with a killing agent; and thereby creating a killed virus vaccine.

16. The method of claim 15, wherein the killing agent is selected from Gamma ray radiation, beta-propiolactone, formaldehyde, and combinations thereof.

17. The method of one of claim 15 or claim 16, wherein the first dialdehyde is glutaraldehyde and the second killing agent is formaldehyde or beta-propiolactone at a final concentration of 2%.

18. The method of one of claim 15 to claim 17, further comprising combining the vaccine with an adjuvant.

19. The method of any one of any one of claims 15-18, wherein the aldehyde is glutaraldehyde at 0.005%.

20. The method of any one of claims 15-19, wherein the di-imidoester is selected from SB3, DMA, DMS, DMP, and combinations thereof.

Greaney, A. J. et al., (2021), Antibodies elicited by mRNA-1273 vaccination bind more broadly to the receptor binding domain than do those from SARS-CoV-2 infection, Sci Transl Med 13(600).

REFERENCES

Piccoli, L. et al., (2020), Mapping Neutralizing and Immunodominant Sites on the SARS-CoV-2 Spike Receptor-Binding Domain by Structure-Guided High-Resolution Serology, November 12; 183(4): 1024-1042.

Reid, B. D. (1998), The Sterways process: a new approach to inactivating viruses using gamma radiation, Biologicals 26(2): 125-129.

All references disclosed herein, whether patent or non-patent, are hereby incorporated by reference as if each was included at its citation, in its entirety. In case of conflict between reference and specification, the present specification, including definitions, will control.

Although the present disclosure has been described with a certain degree of particularity, it is understood the disclosure has been made by way of example, and changes in detail or structure may be made without departing from the spirit of the disclosure as defined in the appended claims.

I claim:

1. A method for preparing a vaccine, the method comprising:
combining a dialdehyde/di-imidoester with a pathogen;
contacting the dialdehyde/di-imidoester with proteins from the pathogen, and allowing the dialdehyde/di-imidoester to form intra-protein bonds to create dialdehyde/di-imidoester-modified pathogen proteins;
removing or reacting dialdehyde/di-imidoester not bonded to protein;
isolating the dialdehyde/di-imidoester-modified pathogen proteins; and
combining the dialdehyde/di-imidoester-modified pathogen proteins with an adjuvant.

2. The method of claim 1, wherein the concentration of protein combined with the dialdehyde/di-imidoester is less than about 1.0 mg/ml.

3. The method of claim 2, wherein the concentration of protein is less than about 0.5 mg/ml.

4. A method of immunizing a subject, the method comprising:
injecting a subject with a dialdehyde/di-imidoester-modified pathogen protein;
injecting the subject a second time with the dialdehyde/di-imidoester-modified pathogen protein.

5. The method of claim 4, wherein the subject is a mammal or avian.

6. The method of claim 5, wherein the subject is selected from a human, a cow, a pig, horse, cat, dog, bird, or chicken.

7. The method of claim 6, wherein the dialdehyde/di-imidoester comprises 4 or more carbons.

8. The method of claim 7, wherein the dialdehyde/di-imidoester comprises a short chain dialdehydes/di-imidoester with 4, 5, 6, 7, 8, 9, or 10 carbons.

9. The method of claim 2, wherein the dialdehyde/di-imidoester is selected from glutaraldehyde, dialdehyde, SB3, DMA, DMS, DMP, or combinations thereof.

10. The method of claim 9, wherein the dialdehyde is glutaraldehyde.

11. The method of claim 2, wherein the pathogen is selected from a virus, bacterium, fungus.

12. The method of claim 11, wherein the pathogen is a virus selected from coronavirus, influenza, retro, or rhino virus.

13. The method of claim 12, wherein the pathogen is influenza.

14. The method of claim 12, wherein the pathogen is SARS-COV-2.

15. A method of creating a vaccine from a virus, comprising:
contacting the virus with a first dialdehyde/di-imidoester;
incubating the virus and the first dialdehyde/di-imidoester for a first time period, to allow viral proteins to cross-link to form a cross-linked mixture;
treating the mixture with a killing agent; and thereby creating a killed virus vaccine.

16. The method of claim 15, wherein the killing agent is selected from Gamma ray radiation, beta-propiolactone, formaldehyde, and combinations thereof.

17. The method of claim 16, wherein the first dialdehyde is glutaraldehyde and the second killing agent is formaldehyde or beta-propiolactone at a final concentration of 2%.

18. The method of claim 17, further comprising combining the vaccine with an adjuvant.

19. The method of claim 15, wherein the aldehyde is glutaraldehyde at 0.005%.

20. The method of claim 15, wherein the di-imidoester is selected from SB3, DMA, DMS, DMP, and combinations thereof.

* * * * *

SEQUENCE LISTING

```
<160> NUMBER OF SEQ ID NOS: 2

<210> SEQ ID NO 1
<211> LENGTH: 130
<212> TYPE: PRT
<213> ORGANISM: Artificial Sequence
<220> FEATURE:
<223> OTHER INFORMATION: SARS-COV-2 (P0DTC2, SPIKE_SARS2, PDB ID: 6MOJ)

<400> SEQUENCE: 1

Leu Asn Asp Leu Cys Phe Thr Asn Val Tyr Ala Asp Ser Phe Val Ile
1               5                   10                  15

Arg Gly Asp Glu Val Arg Gln Ile Ala Pro Gly Gln Thr Gly Lys Ile
            20                  25                  30

Ala Asp Tyr Asn Tyr Lys Leu Pro Asp Asp Phe Thr Gly Cys Val Ile
        35                  40                  45

Ala Trp Asn Ser Asn Asn Leu Asp Ser Lys Val Gly Gly Asn Tyr Asn
    50                  55                  60

Tyr Leu Tyr Arg Leu Phe Arg Lys Ser Asn Leu Lys Pro Phe Glu Arg
65                  70                  75                  80

Asp Ile Ser Thr Glu Ile Tyr Gln Ala Gly Ser Thr Pro Cys Asn Gly
                85                  90                  95

Val Glu Gly Phe Asn Cys Tyr Phe Pro Leu Gln Ser Tyr Gly Phe Gln
            100                 105                 110

Pro Thr Asn Gly Val Gly Tyr Gln Pro Tyr Arg Val Val Val Leu Ser
        115                 120                 125

Phe Glu
    130

<210> SEQ ID NO 2
<211> LENGTH: 129
<212> TYPE: PRT
<213> ORGANISM: Artificial Sequence
<220> FEATURE:
<223> OTHER INFORMATION: SARS-COV (P59594, SPIKE_CVHSA, PDB ID: 2AJF)

<400> SEQUENCE: 2

Leu Asn Asp Leu Cys Phe Ser Asn Val Tyr Ala Asp Ser Phe Val Val
1               5                   10                  15

Lys Gly Asp Asp Val Arg Gln Ile Ala Pro Gly Gln Thr Gly Val Ile
```

-continued

```
                20                  25                  30
Ala Asp Tyr Asn Tyr Lys Leu Pro Asp Asp Phe Met Gly Cys Val Leu
            35                  40                  45

Ala Trp Asn Thr Arg Asn Ile Asp Ala Thr Ser Thr Gly Asn Tyr Asn
    50                  55                  60

Tyr Lys Tyr Arg Tyr Leu Arg His Gly Lys Leu Arg Pro Phe Glu Arg
65                  70                  75                  80

Asp Ile Ser Asn Val Pro Phe Ser Pro Asp Gly Lys Pro Cys Thr Pro
            85                  90                  95

Pro Ala Leu Asn Cys Tyr Trp Pro Leu Asn Asp Tyr Gly Phe Tyr Thr
            100                 105                 110

Thr Thr Gly Ile Gly Tyr Gln Pro Tyr Arg Val Val Val Leu Ser Phe
            115                 120                 125

Glu
```